United States Patent
Carbunaru et al.

(10) Patent No.: US 11,179,568 B2
(45) Date of Patent: Nov. 23, 2021

(54) CONTROLLING CHARGE FLOW IN THE ELECTRICAL STIMULATION OF TISSUE

(71) Applicant: Boston Scientific Neuromodulation Corporation, Valencia, CA (US)

(72) Inventors: Rafael Carbunaru, Valley Village, CA (US); Kelly H. McClure, Valencia, CA (US); Jordi Parramon, Valencia, CA (US)

(73) Assignee: Boston Scientific Neuromodufation Corporation, Valencia, CA (US)

( * ) Notice: Subject to any disclaimer, the term of this patent is extended or adjusted under 35 U.S.C. 154(b) by 413 days.

(21) Appl. No.: 16/056,165

(22) Filed: Aug. 6, 2018

(65) Prior Publication Data
US 2018/0345021 A1 Dec. 6, 2018

Related U.S. Application Data

(63) Continuation of application No. 15/213,076, filed on Jul. 18, 2016, now Pat. No. 10,065,039, which is a
(Continued)

(51) Int. Cl.
*A61N 1/36* (2006.01)
*A61N 1/372* (2006.01)

(52) U.S. Cl.
CPC ..... *A61N 1/36146* (2013.01); *A61N 1/36103* (2013.01); *A61N 1/36107* (2013.01); *A61N 1/37247* (2013.01); *A61N 1/37264* (2013.01)

(58) Field of Classification Search
CPC .......... A61N 1/3925; A61N 1/08; A61N 1/05; A61N 1/37247; A61N 1/3981; A61N 1/3787; A61N 1/37252; A61N 1/3912; A61N 1/3937; A61N 2001/083; A61N 1/025; A61N 1/36125; A61N 1/36153; A61N 1/37235; A61B 5/0031;
(Continued)

(56) References Cited

U.S. PATENT DOCUMENTS 3,563,247 A 2/1971 Bowers
3,628,538 A 12/1971 Vincent
(Continued)

FOREIGN PATENT DOCUMENTS

WO 01/82398 11/2001
WO 03/005465 1/2003
(Continued)

OTHER PUBLICATIONS

Agnew et al. "Histopathologic Evaluation of Prolonged Intracortical Eletrical Stimulation," Exp. Neur. 92:162-185 (1986).
(Continued)

*Primary Examiner* — Deborah L Malamud
(74) *Attorney, Agent, or Firm* — Lewis & Reese, PLLC

(57) ABSTRACT

Systems of techniques for controlling charge flow during the electrical stimulation of tissue. In one aspect, a method includes receiving a charge setting describing an amount of charge that is to flow during a stimulation pulse that electrically stimulates a tissue, and generating and delivering the stimulation pulse in a manner such that an amount of charge delivered to the tissue during the stimulation pulse accords with the charge setting.

18 Claims, 10 Drawing Sheets

Related U.S. Application Data continuation of application No. 12/836,440, filed on Jul. 14, 2010, now Pat. No. 9,393,421, which is a continuation of application No. 11/139,296, filed on May 26, 2005, now Pat. No. 7,801,600.

(58) Field of Classification Search
CPC ...... A61M 2205/3523; A61M 5/14276; A61M 2205/3507; G06F 19/3418
See application file for complete search history.

(56) References Cited

U.S. PATENT DOCUMENTS

| | | |
|---|---|---|
| 3,751,605 A | 8/1973 | Michelson |
| 3,850,161 A | 11/1974 | Liss |
| 3,881,495 A | 5/1975 | Pannozzo et al. |
| 4,232,679 A | 11/1980 | Schulman |
| 4,408,608 A | 10/1983 | Daly et al. |
| 4,480,830 A | 11/1984 | Petrofsky et al. |
| 4,481,950 A | 11/1984 | Duggan |
| 4,590,946 A | 5/1986 | Loeb |
| 4,608,985 A | 9/1986 | Crish et al. |
| 4,628,942 A | 12/1986 | Sweeney et al. |
| 4,649,936 A | 3/1987 | Ungar et al. |
| 4,690,145 A | 9/1987 | King-Smith et al. |
| 4,702,254 A | 10/1987 | Zabara |
| 4,793,353 A | 12/1988 | Borkan |
| 5,188,104 A | 2/1993 | Wernicke et al. |
| 5,193,539 A | 3/1993 | Schulman et al. |
| 5,193,540 A | 3/1993 | Schulman et al. |
| 5,211,129 A | 5/1993 | Taylor et al. |
| 5,215,086 A | 6/1993 | Terry, Jr. et al. |
| 5,222,494 A | 6/1993 | Baker, Jr. |
| 5,299,569 A | 4/1994 | Wernicke et al. |
| 5,305,445 A | 4/1994 | Nishikawa |
| 5,305,745 A | 4/1994 | Zacouto |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,358,514 A | 10/1994 | Schulman et al. |
| 5,468,254 A | 11/1995 | Hahn et al. |
| 5,501,703 A | 3/1996 | Holsheimer et al. |
| 5,513,636 A | 5/1996 | Palti |
| 5,515,848 A | 5/1996 | Corbett, III et al. |
| 5,571,148 A | 11/1996 | Loeb et al. |
| 5,700,282 A | 12/1997 | Zabara |
| 5,716,318 A | 2/1998 | Manning |
| 5,752,979 A | 5/1998 | Benabid |
| 5,755,750 A | 5/1998 | Petruska et al. |
| 5,895,416 A | 4/1999 | Barreras, Sr. et al. |
| 5,938,688 A | 8/1999 | Schiff |
| 5,941,906 A | 8/1999 | Barreras, Sr. |
| 5,995,868 A | 11/1999 | Dorfineister et al. |
| 6,016,449 A | 1/2000 | Fischell et al. |
| 6,035,237 A * | 3/2000 | Schulman .......... A61N 1/36125 607/2 |
| 6,051,017 A | 4/2000 | Loeb et al. |
| 6,104,956 A | 8/2000 | Naritoku et al. |
| 6,112,116 A | 8/2000 | Fischell et al. |
| 6,154,678 A | 11/2000 | Lauro |
| 6,164,284 A | 12/2000 | Schulman et al. |
| 6,178,349 B1 | 1/2001 | Kieval |
| 6,185,452 B1 | 2/2001 | Schulman et al. |
| 6,205,359 B1 | 3/2001 | Boveja |
| 6,208,894 B1 | 3/2001 | Schulman et al. |
| 6,216,045 B1 | 4/2001 | Black et al. |
| 6,219,580 B1 | 4/2001 | Faltys et al. |
| 6,266,564 B1 | 7/2001 | Hill et al. |
| 6,272,382 B1 | 8/2001 | Faltys et al. |
| 6,280,873 B1 | 8/2001 | Tsukamoto |
| 6,341,236 B1 | 1/2002 | Osorio et al. |
| 6,381,496 B1 | 4/2002 | Meadows et al. |
| 6,393,326 B1 | 5/2002 | Nachum |
| 6,458,171 B1 | 10/2002 | Tsukamoto |
| 6,487,446 B1 | 11/2002 | Hill et al. |
| 6,516,227 B1 | 2/2003 | Meadows et al. |
| 6,526,318 B1 | 2/2003 | Ansarinia |
| 6,539,263 B1 | 3/2003 | Schiff et al. |
| 6,553,263 B1 | 4/2003 | Meadows et al. |
| 6,560,490 B2 | 5/2003 | Grill et al. |
| 6,582,441 B1 | 6/2003 | He et al. |
| 6,597,954 B1 | 7/2003 | Pless et al. |
| 6,643,549 B1 | 11/2003 | Bradley et al. |
| 6,712,753 B2 | 3/2004 | Manne |
| 6,760,626 B1 | 7/2004 | Boveja |
| 6,782,292 B2 | 8/2004 | Whitehurst |
| 6,826,428 B1 | 11/2004 | Chen et al. |
| 6,907,295 B2 | 6/2005 | Gross et al. |
| 6,928,320 B2 | 8/2005 | King |
| 7,054,689 B1 | 5/2006 | Whitehurst et al. |
| 7,200,504 B1 | 4/2007 | Fister |
| 7,203,548 B2 | 4/2007 | Whitehurst et al. |
| 7,242,985 B1 | 7/2007 | Fridman et al. |
| 7,277,760 B1 | 10/2007 | Litvak et al. |
| 7,292,890 B2 | 11/2007 | Whitehurst et al. |
| 7,308,303 B2 | 12/2007 | Whitehurst et al. |
| 7,450,994 B1 | 11/2008 | Mishra et al. |
| 7,522,961 B2 | 4/2009 | Fridman et al. |
| 7,599,500 B1 | 10/2009 | Segel et al. |
| 7,702,396 B2 | 4/2010 | Litvak et al. |
| 7,729,775 B1 | 6/2010 | Saoji et al. |
| 7,899,539 B2 | 3/2011 | Whitehurst et al. |
| 8,027,733 B1 | 9/2011 | Fridman et al. |
| 2001/0003799 A1 | 6/2001 | Boveja |
| 2001/0046625 A1 | 11/2001 | Ruth et al. |
| 2001/0053476 A1 | 12/2001 | Ruth et al. |
| 2002/0016615 A1 | 2/2002 | Dev et al. |
| 2002/0022873 A1 | 2/2002 | Erickson et al. |
| 2003/0083698 A1 | 5/2003 | Whitehurst et al. |
| 2003/0125773 A1 * | 7/2003 | Havel ................ A61N 1/3906 607/7 |
| 2003/0203890 A1 | 10/2003 | Steiner et al. |
| 2003/0236557 A1 | 12/2003 | Whitehurst et al. |
| 2003/0236558 A1 | 12/2003 | Whitehurst et al. |
| 2004/0010290 A1 | 1/2004 | Schroeppel |
| 2004/0015204 A1 | 1/2004 | Whitehurst et al. |
| 2004/0015205 A1 | 1/2004 | Whitehurst et al. |
| 2004/0172089 A1 | 9/2004 | Whitehurst et al. |
| 2004/0243182 A1 | 12/2004 | Cohen et al. |
| 2005/0021108 A1 | 1/2005 | Klosterman et al. |
| 2005/0101878 A1 | 5/2005 | Daly et al. |
| 2005/0137651 A1 | 6/2005 | Litvak |
| 2005/0245971 A1 | 11/2005 | Brockway et al. |
| 2006/0100672 A1 | 5/2006 | Litvak |
| 2006/0106446 A1 | 5/2006 | Fridman |
| 2006/0229688 A1 | 10/2006 | McClure et al. |
| 2007/0021800 A1 | 1/2007 | Whitehurst et al. |
| 2007/0055308 A1 | 3/2007 | Haller et al. |
| 2007/0123938 A1 | 5/2007 | Haller et al. |
| 2007/0260292 A1 | 11/2007 | Faltys et al. |
| 2010/0292759 A1 | 11/2010 | Hahn et al. |
| 2010/0331913 A1 | 12/2010 | Mann et al. |
| 2011/0040350 A1 | 2/2011 | Griffith |
| 2011/0077579 A1 | 3/2011 | Harrison et al. |

FOREIGN PATENT DOCUMENTS

| | | |
|---|---|---|
| WO | 2006/053101 | 5/2006 |
| WO | 2007/030496 | 3/2007 |

OTHER PUBLICATIONS

Lapicque L. "[Quantitative Research on the Electrical Exitation of Nerves Treated as a Polarization]" J. Phys. Gen. Path. 1: 620-635 (1907) [French]—Certified English Translation Attached.

McCreery et al. "Charge Density and Charge Per Phase as Cofactors in Neural Injury Induced by Electrical Stimulation" IEEE Transactions on Biomedical Engineering 37(10):996-1001 (1990).

McNeal D. "Analysis of a Model for Excitation of Myelinated Nerve" IEEE Transactions on Biomedical Engineering 23 (4):329-337 (1976).

(56) References Cited

OTHER PUBLICATIONS

Pudenz et al. "Electrical Stimulation of the Brain: Effects on the Blood Brain Barrier" Surg. Neurol. 4:265-270 (1975).

* cited by examiner

CONTROLLING CHARGE FLOW IN THE ELECTRICAL STIMULATION OF TISSUE

CROSS REFERENCE TO RELATED APPLICATIONS

This is a continuation of U.S. patent application Ser. No. 15/213,076, filed Jul. 18, 2016 (allowed), which is a continuation of U.S. Non-Provisional patent application Ser. No. 12/836,440, filed Jul. 14, 2010 (now U.S. Pat. No. 9,393,421), which is a continuation of U.S. Non-Provisional patent application Ser. No. 11/139,296, filed May 26, 2005 (now U.S. Pat. No. 7,801,600). Priority is claimed to these applications, and they are incorporated herein by reference in their entireties.

BACKGROUND

This disclosure relates to controlling the flow of charge in the electrical stimulation of tissue.

Tissues can be electrically stimulated directly or indirectly to elicit a desired response. Direct stimulation involves the provision of one or more electrical stimuli directly to the stimulated tissue. Indirect stimulation involves the provision of one or more electrical stimuli to adjacent or otherwise related tissue, where the related tissue causes the desired response to be elicited from the stimulated tissue. The desired response can be, e.g., inhibitory or excitatory. Inhibitory responses tend to discourage certain behavior by the stimulated tissue, whereas excitatory responses tend to encourage certain behavior by the stimulated tissue. Encouraged or discouraged behaviors can include cellular depolarization, the release of chemical species, and/or the inhibition of cellular depolarization.

Electrical stimuli can be used by medical devices to stimulate tissue in a number of different settings, including therapeutic, diagnostic, and functional settings. In such settings, electrical stimulation often is provided in accordance with stimulation parameters. The stimulation parameters characterize the electrical stimuli for purposes of delivery.

SUMMARY

Systems and techniques relating to controlling charge flow in the electrical stimulation of tissue are described. In one aspect, a method includes receiving a charge setting describing an amount of charge that is to flow during a stimulation pulse that electrically stimulates a tissue, and generating and delivering the stimulation pulse in a manner such that an amount of charge delivered to the tissue during the stimulation pulse accords with the charge setting.

This and other aspects can include one or more of the following features. A stimulation waveform that includes the stimulation pulse and a secondary pulse can be generated. The secondary pulse can reduce accumulation of charge at an electrode that has delivered the stimulation pulse. The charge setting can be received from a user. The delivery of the stimulation pulse can include monitoring the flow of charge during delivery of the stimulation pulse, and halting the delivery based on the amount of charge described by the charge setting. The delivery can be halted based on the flow of charge exceeding the amount of charge described by the charge setting.

The delivery of the stimulation pulse can include changing, based on the charge setting, one or more stimulation parameters that characterize one or more aspects of a stimulation waveform that includes the stimulation pulse, and delivering the stimulation waveform in accordance with the stimulation parameters. The stimulation parameters can be changed by converting the charge setting into the one or more stimulation parameters. The charge setting can be converted by calculating a stimulation pulse duration using a stimulation pulse amplitude or by accessing a data compilation using the charge setting to identify at least one of a predetermined stimulation pulse duration and a predetermined stimulation pulse amplitude. The charge setting can also be converted by holding a stimulation pulse amplitude substantially constant for two or more different charge settings and determining a stimulation pulse duration based on the received charge setting and the substantially constant stimulation pulse amplitude. Holding the stimulation pulse amplitude substantially constant can include accessing a data compilation that associates a substantially constant stimulation pulse amplitude with the two or more charge settings.

The charge setting can also be converted into the one or more stimulation parameters by holding a stimulation pulse duration substantially constant for another two or more different charge settings, and determining a stimulation pulse amplitude based on the received charge setting and the substantially constant stimulation pulse duration. The settings for which stimulation pulse amplitude is held substantially constant can be discrete charge settings that describe relatively smaller amounts of charge flow. The charge settings for which stimulation pulse duration is held substantially constant can be discrete charge settings that describe relatively larger amounts of charge flow. There can be no charge settings intermediate between the charge settings for which stimulation pulse amplitude is held substantially constant and the charge settings for which stimulation pulse duration is held substantially constant. Holding the stimulation pulse amplitude substantially constant can include accessing a data compilation that associates each of a plurality of substantially constant voltage steps with two or more charge settings.

In another aspect, a method includes receiving a charge boundary describing a largest amount of charge that is to flow in a stimulation pulse of an electrical stimulation waveform, receiving a change to the stimulation waveform, determining that the received change to the stimulation waveform would cause the stimulation pulse to violate the charge boundary, and accommodating the change to the stimulation waveform based on the determination. The stimulation pulse is to electrically stimulate tissue when delivered over an electrode.

This and other aspects can include one or more of the following features. A charge setting describing a proposed amount of charge to be delivered in the stimulation pulse can be received. The charge boundary can be compared to the received charge setting to determine that the received change to the stimulation waveform would cause the stimulation pulse to violate the charge boundary. The change to the stimulation waveform can be received at an extracorporeal portion of a system that includes an implanted stimulator.

The accommodation of the change to the stimulation waveform can include rejecting the change to the stimulation waveform or changing the stimulation waveform so that the amount of charge to flow in the stimulation pulse accords with the amount of charge identified by the charge boundary. The stimulation waveform can be changed by converting the charge boundary into one or more stimulation parameters or by halting a stimulation pulse when the amount of charge does not accord with the amount of charge described by the charge boundary. The change to a stimulation waveform can be received when the waveform is actively being delivered to electrically stimulate the tissue.

In another aspect, a system includes a user interface configured to interact with a user to receive a charge setting describing an amount of charge that is to flow in the electrical stimulation of tissue, a converter configured to convert the received charge setting into one or more stimulation parameters, the stimulation parameters characterizing aspects of a stimulation waveform that is to be delivered to stimulate the tissue, a signal generator that is programmable to generate the stimulation waveform in accordance with the stimulation parameters, and an electrode arranged to receive the stimulation waveform from the signal generator and to deliver the stimulation waveform to stimulate the tissue.

This and other aspects can include one or more of the following features. The system can include an implantable stimulator that includes the signal generator and the electrode. The implantable stimulator can include the converter. The converter can be a data processing device configured to perform at least a portion of the conversion of the charge setting in accordance with logic of a set of machine-readable instructions.

The converter can include a memory device that associates individual charge settings with collections of the changes to the stimulation parameters and/or special purpose logic circuitry to perform at least a portion of the conversion. The user interface can be configured to receive a first charge setting that specifies a relative change in the amount of charge that is to flow in the electrical stimulation of tissue or to receive a first charge setting that directly specifies the amount of charge that is to flow in the electrical stimulation of tissue.

The user interface can also be configured to receive a first charge setting that identifies an incremental increase or a decremental decrease in the amount of charge that is to flow in the electrical stimulation of tissue. The user interface can be configured to interact with a user to receive a charge boundary describing a largest amount of charge that is to flow in a stimulation pulse for the electrical stimulation of tissue.

The system can also include a comparator to compare the one or more stimulation parameters with the charge boundary to ensure that the stimulation waveform would not violate the charge boundary. The comparator can compare the charge setting with the charge boundary to ensure that the stimulation waveform would not violate the charge boundary.

In another aspect, a system for controlling charge flow during electrical stimulation of tissue includes a waveform generator configured to generate a waveform to electrically stimulate the tissue, a receiver configured to receive a charge setting specifying an amount of charge to be delivered in the electrical stimulation of tissue, and a coulomb counter configured and arranged to measure an amount of charge delivered in a stimulation pulse and to generate the trigger when the amount of charge delivered accords with that specified by the charge setting. The waveform generator is programmable to end the generation of a stimulation pulse based on receipt of a trigger. The waveform generator includes a trigger input to receive the trigger. The coulomb counter includes a trigger output to convey the trigger to the trigger input of the programmable waveform generator.

This and other aspects can include one or more of the following features. The system can include an implantable stimulator that includes the waveform generator and the coulomb counter. The implantable stimulator can also include the receiver. The receiver can be a wireless data receiver configured to receive a wireless signal that includes the charge setting. The receiver can include an extracorporeal user interface configured to receive the charge setting from a human user. The system can also include step-up circuitry configured to increase a voltage for the stimulation pulse above a supply voltage of the waveform generator.

The details of one or more implementations are set forth in the accompanying drawings and the description below. Other features and advantages will be apparent from the description, drawings, and claims.

BRIEF DESCRIPTION OF THE DRAWINGS

Like reference symbols in the various drawings indicate like elements.

DETAILED DESCRIPTION

Figure 1:
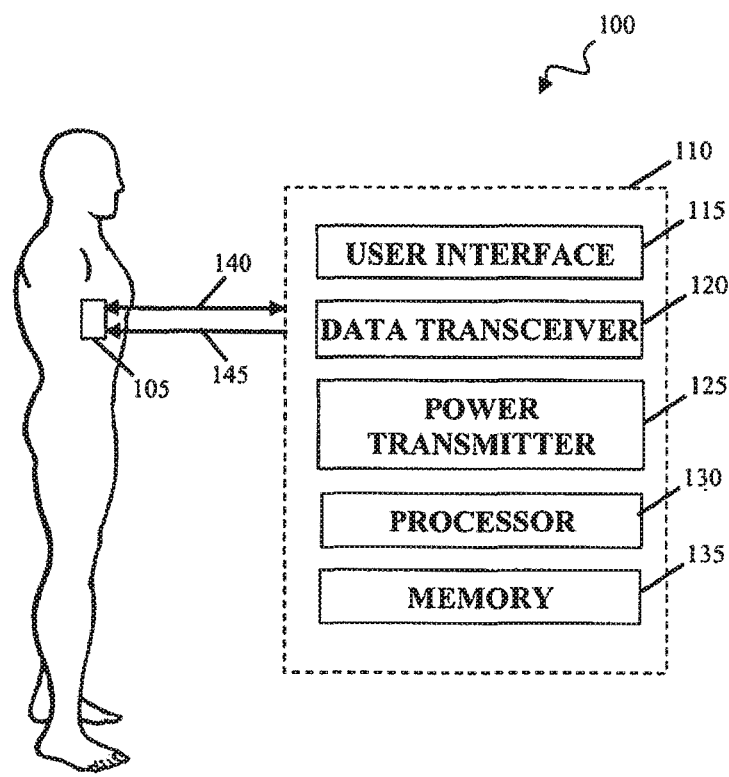
FIG. 1 shows a system in which charge flow during stimulation can be controlled.

FIG. 1 shows a system 100 in which charge flow during stimulation can be controlled. System 100 can include an implanted portion 105 and an external (i.e., extracorporeal) portion 110. Implanted portion 105 is a device that is adapted for implantation in a body. For example, implanted portion 105 can include a biocompatible housing adapted to reduce the immune response and/or cell necrosis associated with the implantation of portion 105. Implanted portion 105 can stimulate tissue. For example, implanted portion 105 can electrically excite the depolarization of a nerve and/or muscle tissue for therapeutic, diagnostic, and/or functional purposes. As discussed further below, implanted portion 105 can include one or more elements to deliver electrical stimuli to tissue.

In some implementations, implanted portion 105 can be implanted in a body with one or more surgical insertion tools tailored for the implantation of portion 105. Alternatively, implanted portion 105 can be implanted using commercially available surgical equipment, such as hypodermic needles, conventional surgical equipment, and endoscopic or laparoscopic devices.

In some implementations, implanted portion 105 can operate independently (i.e., as a solitary implanted device) or implanted portion 105 can operate as part of an implanted system of devices whose activities are coordinated to achieve therapeutic, diagnostic, and/or functional purposes.

In some implementations, implanted portion 105 can receive data from one or more sensing devices (not shown) that respond to one or more conditions of the body in which implanted portion 105 is implanted. Example sensing devices include chemical sensors, electrodes, optical sensors, mechanical (e.g., motion, pressure) sensors, and temperature sensors. The received data can be used by implanted portion 105 in controlling the electrical stimulation of tissue.

External (extracorporeal) portion 110 is a device for providing user interaction with implanted portion 105. External portion 110 is generally situated outside the body in which implanted portion 105 is implanted. External portion 110 can include a user interface 115, a data transceiver 120, a power transmitter 125, a processor 130, and a memory 135. User interface 115, data transceiver 120, power transmitter 125, processor 130, and memory 135 can be housed in a single housing or in multiple housings. User interface 115, data transceiver 120, power transmitter 125, processor 130, and memory 135 can be linked for data communication and control by one or more wired (e.g., wires, busses, optical fiber) or wireless (e.g., infrared, WiFi, sound, magnetic, electromagnetic, radio frequency (RF)) data links.

User interface 115 can include one or more input/output devices for interacting with a user. For example, input/output devices can be mechanical, audio, and/or visual devices, including keypads, touch- and display-screens, speakers, and data ports.

Data transceiver 120 communicates with implanted portion 105 over a data link 140. This communication can include both the transmission and reception of data, including data that represents commands received from a user over user interface 115 and data regarding the operational status and history of implanted portion 105. For example, data that represents a charge setting, a charge boundary, boundaries on stimulation parameters, the current operational settings of stimulation parameters, and whether or not implanted portion 110 is actively stimulating tissue can be communicated over data link 140.

Data transceiver 120 includes both a transmitter and a receiver. Data transceiver 120 can be a wireless transceiver in that transceiver 120 communicates with implanted portion 105 without the use of a transdermal physical link. For example, data transceiver 120 can communicate with implanted portion 105 using sound and/or electromagnetic radiation (e.g., light or radio waves) that propagates through a body to and from implanted portion 105.

Power transmitter 125 relays energy to implanted portion 105 over a power link 145. The energy relayed from transmitter 125 can be captured and stored in implanted portion 105 and subsequently converted into one or more stimuli for stimulating tissue. The relayed energy can include electrical energy, magnetic energy, electromagnetic energy, and/or mechanical energy. Power transmitter 125 can be a wireless transmitter in that transmitter 125 relays energy to implanted portion 105 without the use of a transdermal physical link.

Processor 130 is a data processing device that performs processing activities in accordance with logic established by a set of instructions. The logic can be embodied in hardware and/or software. For example, the processor 130 can be a microprocessor, ASIC's, FPGA's, and/or a set of logic elements arranged to embody the logic.

The logic of processor 130 can implement operations associated with controlling the electrical stimulation of tissue. These operations can include the management of interactions with a user over user interface 115, the communication of data with implanted portion 105 over data transceiver 120, and the relaying of energy to implanted portion 105 over power transmitter 125. These operations can also include various processes described below.

Memory 135 is a storage device that can store instructions and/or data for controlling the stimulation of tissue in machine-readable format. Memory 135 can be accessed by one or more of user interface 115, data transceiver 120, power transmitter 125, and processor 130 to store and/or retrieve instructions and/or data. Memory 135 can include a memory controller or other interface to facilitate such exchanges of information.

Figure 2:
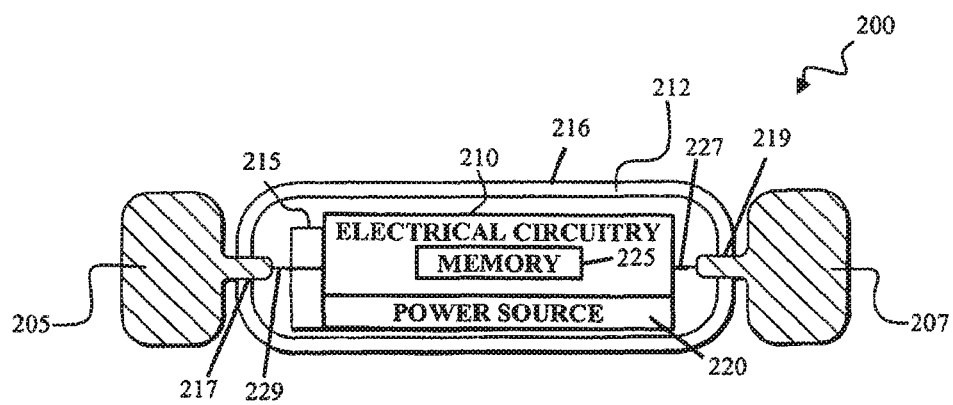
FIG. 2 shows one implementation of an implanted portion of the system of FIG. 1.

FIG. 2 shows one implementation of implanted portion 105, namely an electrical stimulator 200. Stimulator 200 includes a pair of electrodes 205, 207 mounted on a narrow, elongate capsule 212. The outer surface 216 of capsule 212 can be made, at least in part, of a biocompatible material such as biocompatible polymers, glasses, metals, and/or other ceramics. Capsule 212 can be sealed to exclude water but permit passage of electromagnetic fields used to transmit data and/or power.

In various implementations, capsule 212 can have a diameter of less than about 4-5 mm, or less than about 3.5 mm. Similarly, capsule 212 can have a length of less than about 30-40 mm, less than about 20-30 mm, or less than about 20 mm. The shape of the capsule 212 can be tailored to the desired target, the surrounding area, and the method of surgical insertion. Shapes other than the thin, elongated cylinder with electrodes at the ends as shown in FIG. 2, such as disks, helical, asymmetrical, or ovoid structures, are possible.

Each electrode 205, 207 traverses the wall of capsule 212 at a respective of openings 217, 219. Electrode 205 can be a stimulating electrode that electrically stimulates tissue, and electrode 207 can be an indifferent electrode that completes the electrical circuit for the stimulating waveform. Electrodes 205, 207 can be made of a conducting ceramic, conducting polymer, and/or a noble or refractory metal, such as gold, silver, platinum, iridium, tantalum, titanium, niobium or their alloys that minimize corrosion, electrolysis, and damage the surrounding tissues.

Capsule 212 houses electronic circuitry 210, a data transceiver 215, and a power source 220. Electronic circuitry 210 can control and/or perform operations in stimulator 200, including the receipt of data and/or power, the decoding and storing data, the generation of electrical stimulation pulses, as well as all or portions of the processes described below.

Electronic circuitry 210 includes a memory 225 and is connected to electrodes 205, 207 by electrical leads 227, 229. Memory 225 is a storage device that can store instructions and/or data for controlling the stimulation of tissue. Electrical leads 227, 229 can be short, flexible leads. For example, leads can be shorter than about 100-150 mm.

Data transceiver 215 includes both a transmitter and a receiver to transmit and receive data from outside of stimulator 200. For example, transceiver 215 can communicate over data link 140 with data transceiver 120 in external portion 110 (FIG. 1).

Power source 220 can supply and store electrical energy for use by stimulator 200. Power source 220 can include a power storage device such as battery or capacitor. Power source 220 can also include a power receiver portion that receives power from outside of stimulator 200, such as an RF link. For example, power source 220 can receive power transmitted over power link 145 from power transmitted 125 in external portion 110 (FIG. 1).

In one implementation of stimulator 200, stimulator 200 is able to generate:

anodic stimulation pulses and cathodic secondary pulses;

a maximum cathodic current of 30 mA, a maximum cathodic current of 8 mA, or a maximum cathodic current of 3 mA;

a maximum cathodic compliance voltage of 30 V, a maximum cathodic compliance voltage of 12 V, or a maximal cathodic compliance voltage of 3 V;

a maximum anodic current of 10 mA, a maximum anodic current of 5 mA, or a maximum anodic current of 0.5 mA;

a maximum anodic compliance voltage of 10 V, a maximum anodic compliance voltage of 5 V, or a maximal anodic compliance voltage of 1 V;

cathodic and anodic pulse widths of between 0.05 and 10.0 msec, pulse widths of between 0.05 and 2.0 msec, or pulse widths of between 0.1 and 0.5 msec; and a stimulation frequency of between 1 and 200 pulses/second, or a stimulation frequency of between 5 and 50 pulses/second.

In other implementations, stimulator 200 can generate pulses with stimulation parameters outside these ranges. In other implementations, stimulator 200 can generate cathodic stimulation pulses and anodic secondary pulses with corresponding characteristics.

Other configurations of stimulator 200 are possible. For example, stimulator 200 can be a BION® microstimulator (Advanced Bionics® Corporation, Valencia, Calif.). Various details associated with the manufacture, operation, and use of BION implantable microstimulators are described in U.S. Pat. Nos. 5,193,539, 5,193,540, 5,312,439, 6,185,452, 6,164,284, 6,208,894, and 6,051,017, the contents of all of which are incorporated herein by reference.

In other implementations, stimulator 200 can include an implantable pulse generator (IPG) coupled to a lead of electrodes, a spinal cord stimulator (SCS), a cochlear implant, a deep brain stimulator, or any other type of implantable stimulator configured to deliver electrical stimuli. Example IPG's include those described in U.S. Pat. Nos. 6,381,496, 6,553,263, and 6,760,626, the contents of all of which are incorporated herein by reference.

Example spinal cord stimulators include those described in U.S. Pat. Nos. 5,501,703, 6,487,446, and 6,516,227, the contents of all of which are incorporated herein by reference. Example cochlear implants include those described in U.S. Pat. Nos. 6,219,580, 6,272,382, and 6,308,101, the contents of all of which are incorporated herein by reference. Example deep brain stimulators include those described in U.S. Pat. Nos. 5,938,688, 6,016,449, and 6,539,263, the contents of all of which are incorporated herein by reference.

Figure 3:
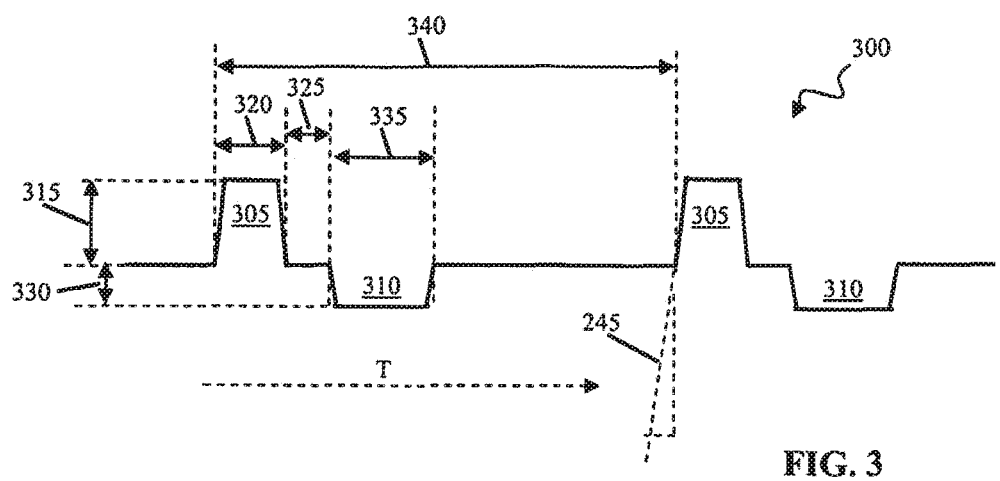
FIG. 3 shows example stimulation parameters that characterize a stimulus waveform.

FIG. 3 shows example stimulation parameters that characterize a stimulus waveform 300. Stimulus waveform 300 is an electrical signal that stimulates tissue. For example, waveform 300 can electrically excite the depolarization of a nerve and/or muscle tissue. Stimulus waveform 300 can be delivered by one or more electrodes in implanted portion 105.

Stimulus waveform 300 can represent either the voltage or the current of electrical stimuli as a function of time T. Stimulus waveform 300 can be a balanced-charge biphasic waveform in that substantial charge does not accumulate at the interface of an electrode that delivers stimulus waveform 300 and electrode corrosion is maintained at an acceptable level. In one implementation, stimulus waveform 300 includes a repetitive series of alternating primary stimulation pulses 305 and secondary recovery pulses 310. Primary stimulation pulses 305 are electrical transients that are adapted to stimulate tissue. Secondary recovery pulses 310 are electrical transients that are adapted to reduce the accumulation of charge at the electrode interface due to primary stimulation pulses 305.

In the illustrated implementation, stimulus waveform 300 is characterized by a primary pulse amplitude parameter 315, a primary pulse duration parameter 320, a delay parameter 325, a secondary pulse amplitude parameter 330, a secondary pulse duration parameter 335, a period parameter 340, and a pulse shape parameter 345.

Primary pulse amplitude parameter 315 characterizes either the voltage or current pulse amplitude of primary stimulation pulses 305 in waveform 300, whereas primary pulse duration parameter 320 characterizes the duration of primary stimulation pulses 305. Primary pulse amplitude parameter 315 is generally given in units of voltage or current, whereas primary pulse duration parameter 320 is generally given in units of time.

Delay parameter 325 characterizes the time between a primary pulse 305 and a secondary pulse 310. The time characterized by delay parameter 325 is generally long enough to prevent secondary pulses 310 from interfering with the stimulation of tissue by primary pulses 305.

Secondary pulse amplitude parameter 330 characterizes either the voltage or current pulse amplitude of secondary recovery pulses 310 in waveform 300, whereas secondary pulse duration parameter 335 characterizes the duration of secondary recovery pulses 310. Secondary pulse amplitude parameter 330 is generally given in units of voltage or current, whereas secondary pulse duration parameter 335 is generally given in units of time.

Period parameter 340 characterizes the time between repetitions of identical portions of stimulus waveform 300. As illustrated, period parameter 340 characterizes the time between successive primary pulses 305 in waveform 300. Period parameter 340 can also be expressed as a pulse rate (e.g., pulses per time). Pulse shape parameter 345 characterizes an aspect of one or more pulses in waveform 300. As illustrated, pulse shape parameter 345 characterizes the rising slope of primary pulses 305, but a variety of other pulses and other aspects of pulses can be characterized by pulse shape parameters.

Stimulus waveform 300 can be tailored to stimulate specific cell populations and exclude others from stimulation. For example, relatively low frequency electrical stimulation (e.g., less than about 50-100 Hz) may have an excitatory effect on an adjacent neural cell, leading to increased neural activity, whereas relatively high frequency electrical stimulation (e.g., greater than about 50-100 Hz) may have an inhibitory effect, leading to decreased neural activity. Similar tailoring can be used to stimulate and exclude other classes of tissues, such as muscle tissue.

Figure 4:
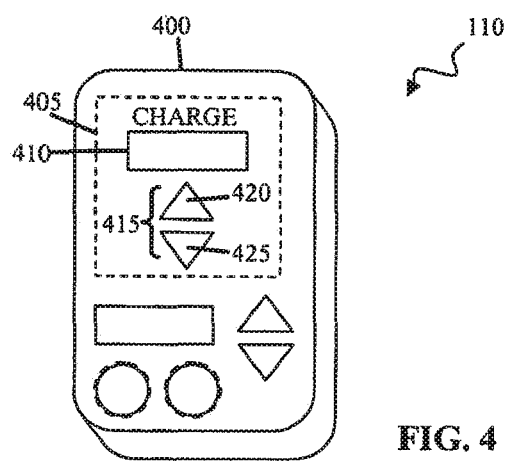
FIG. 4 shows one implementation of a housing of the external portion of the system of FIG. 1.

FIG. 4 shows one implementation of a housing of external portion 110, namely a housing 400. Housing 400 is adapted to shelter certain sensitive components of user interface 115, data transceiver 120, power transmitter 125, processor 130, and memory 135 from the environment while allowing a user to interact with other, less sensitive components.

One collection of components with which a user can interact is a collection of charge setting components 405. Charge setting components 405 interact with a user to allow a user to set the charge delivered by stimulation pulses, such as stimulation pulses 305 in waveform 300 (FIG. 3). Charge is a quantity of electricity and charge delivery in a stimulation pulse is generally the result of the introduction or withdrawal of electrons during the stimulation pulse. Charge can be measured in Coulombs or in other units that can be converted into Coulombs.

The amount of charge actually delivered in a stimulation pulse is related to the characteristics of the stimulation pulse. For example, when primary pulse amplitude parameter 315 characterizes the current amplitude of primary stimulation pulses 305 in waveform 300, the amount of charge actually delivered (Q) can be approximated by:

$$Q \approx \text{(pulse amplitude 315)(pulse duration 320)}. \qquad \text{Equation 1}$$

Equation 1 can adjusted to accommodate various forms of pulse amplitude 315. For example, when pulse amplitude 315 changes over time, Equation 1 can be changed to a time integral that includes the changing pulse amplitude 315.

On the other hand, when primary pulse amplitude parameter 315 characterizes the voltage amplitude of primary stimulation pulses 305 in waveform 300, the amount of charge delivered (Q) depends on the impedance of the stimulating electrode/body interface (Z) and can be approximated by:

$$Q \approx \text{(pulse amplitude 315)(pulse duration 320)}/(Z). \qquad \text{Equation 2}$$

The impedance Z can be determined repeatedly during the operation of a stimulator. Alternatively, the impedance Z can be estimated and programmed into the stimulator and/or external portion. Equation 2 can be adjusted to accommodate various forms of pulse amplitude 315 and impedance Z. For example, when pulse amplitude 315 and/or impedance Z changes over time, Equation 2 can be changed to a time integral that includes the changing pulse amplitude 315 and/or impedance Z.

The impedance Z refers to the electrical impedance of current flow from one electrode through tissue and into another electrode. Electrical impedance can vary over time with changes in the electrodes and/or surrounding tissue. For example, the location of an electrode within a moving body can vary over time, the electrical characteristics of tissue at the site of stimulation can vary over time, or the electrode can become contaminated (e.g., biofouling) or otherwise change over time.

The collection of charge setting components 405 includes an output element 410 and input elements 415. Output element 410 is a device that conveys information to a user. Output element 410 can convey information (such as a current charge setting and proposed changes to the charge setting) visually. For example, output element 410 can be an LCD, a mechanical display, and/or an LED display. Output element 410 can also convey information non-visually. For example, output element 410 can be a speaker or a vibrating element.

Input elements 415 are devices that receive information from a user. Input elements 415 can receive information (such as changes to the charge setting) mechanically. For example, input elements 415 can be a pair of pushbuttons 420, 425. Pushbutton 420 allows a user to increase a charge setting by an incremental step. Pushbutton 425 allows a user to decrease a charge setting by an decremental step.

After receipt, a charge setting can be stored and/or inspected to determine if the charge setting is appropriate. Determining if a charge setting is appropriate can include comparing the charge setting with one or more charge setting boundary values. A charge setting boundary value can be the highest or lowest allowable and/or possible value of a charge setting. A charge setting boundary value can reflect the technical characteristics of the stimulating device or a charge setting boundary value can be set by a physician or other medical personnel in light of the placement of the stimulator, the purpose of the stimulation, and/or the characteristics of the stimulator (e.g., to reduce corrosion to an acceptable level). For example, a charge setting boundary value can be received over a user interface such as charge setting components 405 (FIG. 4).

Figure 5:
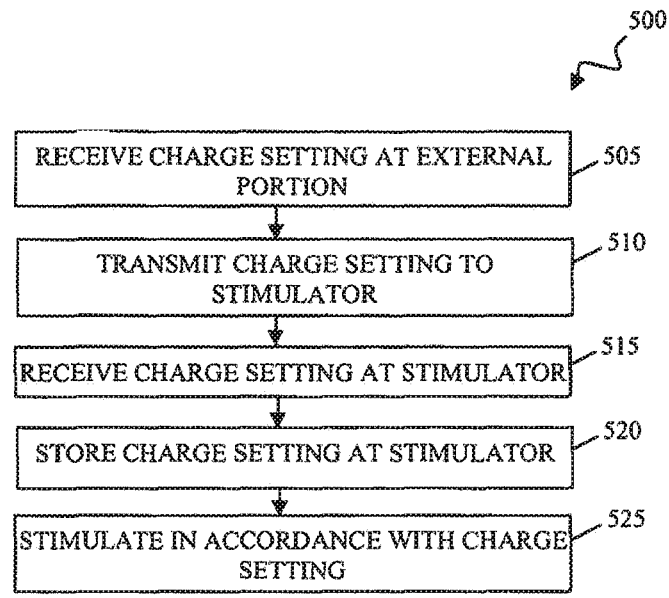
FIG. 5 is a flowchart of a process by which the flow of charge during the electrical stimulation of tissue can be controlled.

FIG. 5 is a flowchart of a process 500 by which the flow of charge during the electrical stimulation of tissue can be controlled. Process 500 can be performed, e.g., by a system for electrically stimulating tissue, such as system 100 (FIG. 1).

The system performing process 500 receives a charge setting at an external portion at 505. The received charge setting can be a change in the charge setting (e.g., an incremental or decremental change) or the received charge setting can be a new value of the charge setting. For example, when process 500 is performed by a system such as system 100, the charge setting can be received over input elements 415 of housing 400 of external portion 110 (FIG. 4).

The received charge setting can be transmitted to a stimulator at 510. For example, the charge setting can be transmitted by a data transceiver 120 over a data link 140 to a data transceiver 215 of an implanted stimulator 200 (FIGS. 1 and 2).

The stimulator receives the charge setting at 515 and stores the charge setting at 520. For example, a charge setting can be received by receiver 215 and stored in a memory such as memory 315 of implanted stimulator 200 (FIG. 2).

The stimulator can stimulate in accordance with the charge setting at 525. Stimulating in accordance with the charge setting includes attempting to ensure that the amount of charge specified by the charge setting is actually introduced or withdrawn during a stimulation pulse.

Figure 6:
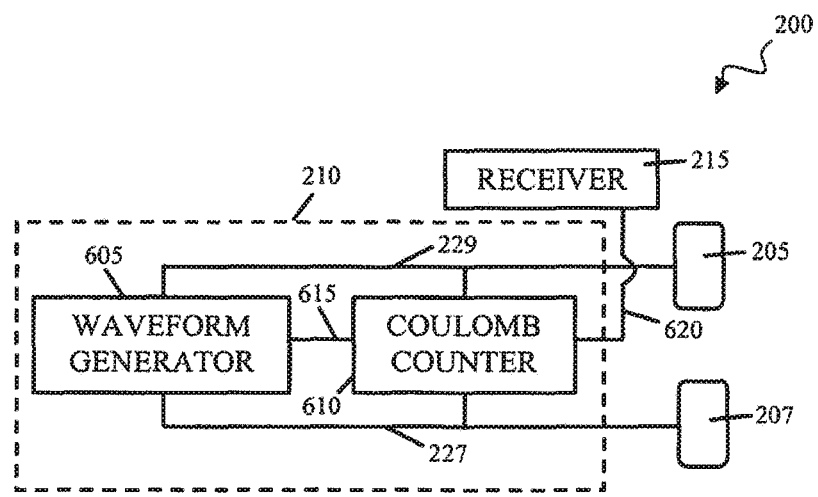
FIG. 6 shows an implementation of the stimulator of FIG. 2 in which charge flow during stimulation can be controlled.

FIG. 6 shows an implementation of a stimulator 200 in which charge flow during stimulation can be controlled. Stimulator 200 includes electrodes 205, 207, receiver 215, leads 229, 227, and electrical circuitry 210. Electrical circuitry 210 includes a waveform generator 605 and a coulomb counter 610. Waveform generator 605 generates a stimulation waveform to stimulate tissue. Waveform generator 605 is connected to electrodes 205, 207 by leads 229, 227 to deliver the stimulation waveform. Electrodes 205, 207 and leads 229, 227 can be electrodes and leads in any system for electrically stimulating tissue. Waveform generator 605 is a programmable waveform generator. For example, in one implementation, the end of a stimulation pulse output by generator 605 can be triggered by an end input received over a control line 615.

Coulomb counter 610 is a device that measures the delivery of charge by electrodes 205, 207 during a stimulation pulse. Coulomb counter 610 can operate, e.g., by measuring a voltage drop across a low impedance series resistance on one or both of leads 229, 227. Coulomb counter 610 is in direct or indirect data communication with receiver 215 over a data path 620. Data path 620 is capable of relaying a charge setting received at receiver 215 to coulomb counter 610. Data path 620 can include memory 325 (not shown).

In operation, stimulator 200 can deliver a stimulation waveform to stimulate tissue in accordance with a charge setting. Such a charge setting can be received by receiver 215 and conveyed along data path 620 to coulomb counter 610. This conveyance can include the storage of the charge setting in a memory and the conversion of the charge setting into a form that is tailored to the operation of coulomb counter 610. For example, when the charge setting is an indication that the delivered charge should be increased by an incremental step, the magnitude of the charge to be delivered (rather than the magnitude or existence of the incremental step) can be conveyed to coulomb counter 610.

Meanwhile, a stimulation waveform such as waveform 300 (FIG. 3) can be generated by waveform generator 605. The stimulation waveform causes charge to be exchanged with the body. This charge passes along the circuit formed by leads 229, 227, electrodes 205, 207, and the body itself. Coulomb counter 610 measures the charge delivered by the stimulation pulses at leads 229, 227. When the charge delivered during a stimulation pulse increases above the charge setting, coulomb counter 610 outputs an end signal to waveform generator 605 over control line 615. The end signal stops the generation of the stimulation pulse, and waveform generator 605 proceeds with the remainder of the stimulation waveform.

Figure 7:
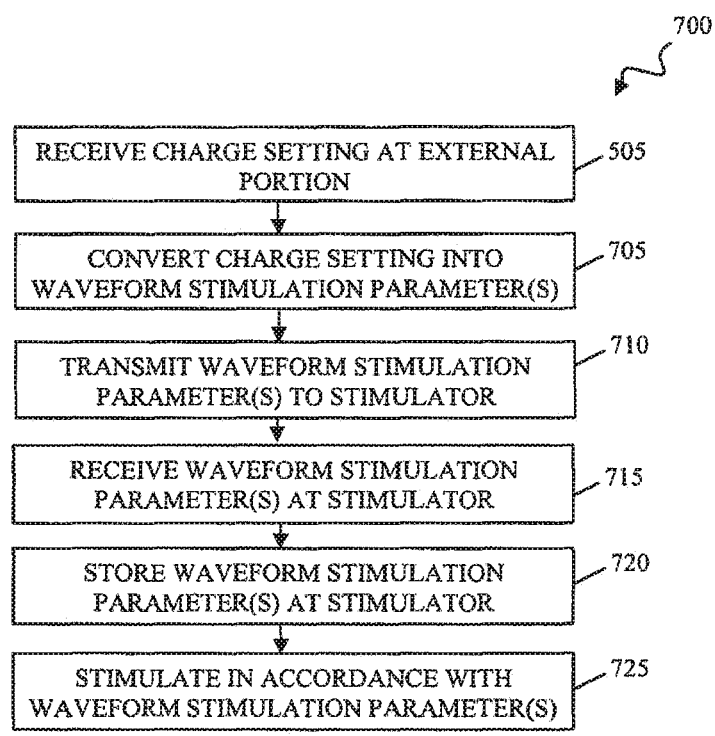
FIGS. 7 and 8 are flowcharts of processes by which the flow of charge during the electrical stimulation of tissue can be controlled.

FIG. 7 is a flowchart of a process 700 by which the flow of charge during the electrical stimulation of tissue can be controlled. Process 700 can be performed, e.g., by a system for electrically stimulating tissue, such as system 100 (FIG. 1).

The system performing process 700 receives a charge setting from a user at an external portion at 505. At the external portion, the system can convert the charge setting into one or more stimulation parameters at 705. The conversion of a charge setting into one or more stimulation parameters can be accomplished in a number of ways. Examples are discussed below, e.g., in FIGS. 10, 11, 12, 17. When system 100 performs process 500, processor 130 can convert the charge setting into one or more stimulation parameters (FIG. 1).

The external portion can then transmit the one or more stimulation parameters to the stimulator at 710. When system 100 performs process 500, data transceiver 120 can transmit the one or more stimulation parameters to implanted portion 105 over data link 140 (FIG. 1).

The stimulator can receive the one or more stimulation parameters from the external portion at 715. The stimulation parameters can be stored at the stimulator at 720. When stimulator 200 is part of the system that performs process 500, data transceiver 215 can receive the parameters and memory 225 can store the parameters (FIG. 2).

The stimulator can also stimulate in accordance with the one or more stimulation parameters at 725. This generally includes the output of electrical waveforms that conform, to some extent, to the stimulation parameters.

Figure 8:
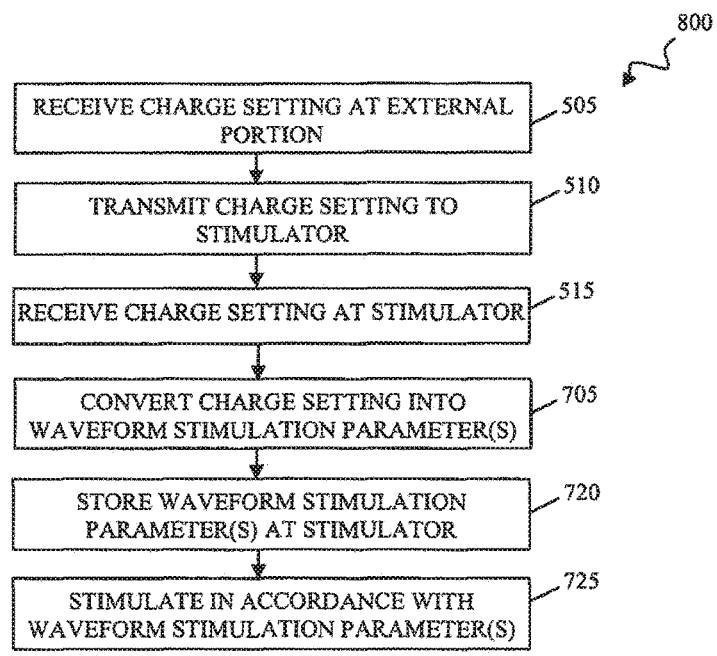

FIG. 8 is a flowchart of a process 800 by which the flow of charge during the electrical stimulation of tissue can be controlled. Process 800 can be performed, e.g., by a system for electrically stimulating tissue, such as system 100 (FIG. 1).

The system performing process 700 receives a charge setting from a user at an external portion at 505. The received charge setting can be transmitted to a stimulator at 510. The stimulator receives the charge setting at 515. For example, the charge setting can be transmitted by a data transceiver 120 over a data link 140 to a data transceiver 215 of an implanted stimulator 200 (FIGS. 1 and 2).

At the stimulator, the system can convert the charge setting into one or more stimulation parameters at 705. The conversion of a charge setting into one or more stimulation parameters can be accomplished in a number of ways, e.g., as discussed below in FIGS. 10, 11, 12, 17. When stimulator 200 is included in the system that performs process 500, electrical circuitry 210 can convert the charge setting into one or more stimulation parameters (FIG. 2).

The stimulation parameters can be stored at the stimulator at 720, and the stimulator can stimulate in accordance with the stimulation parameters at 725. When stimulator 200 is part of the system that performs process 500, memory 225 can store the parameters (FIG. 2).

Figure 9:
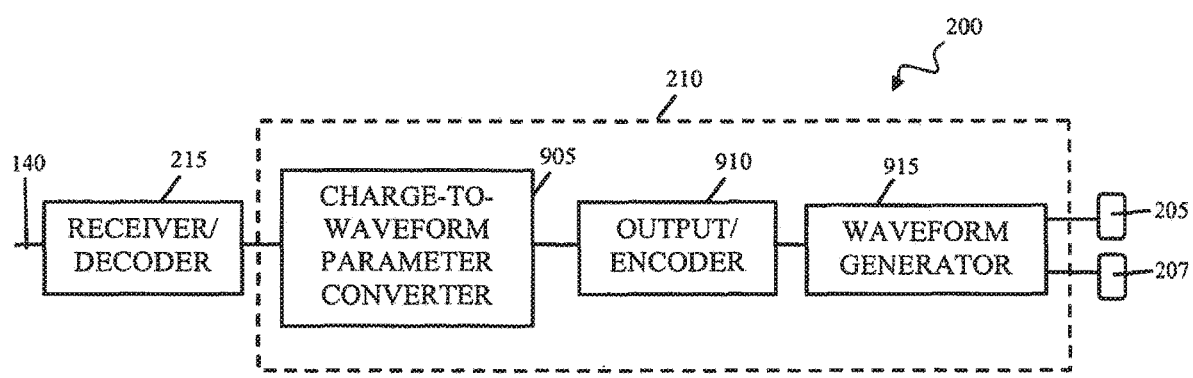
FIG. 9 shows a block diagram of circuitry that can convert a charge setting into a stimulation parameter.

FIG. 9 shows a block diagram of an arrangement of electrical circuitry 210 that can convert a charge setting into one or more stimulation parameters. Electrical circuitry 210 includes a charge-to-waveform parameter converter 905, a output/encoder 910, and a waveform generator 915. Charge-to-waveform parameter converter 905 implements logic for the conversion of a charge setting into one or more stimulation parameters. The logic can be embodied in and/or implemented by hardware and/or software. Charge-to-waveform parameter converter 905 can thus include a data processor, a memory interface, logic elements, and/or special purpose logic circuitry such as one or more FPGA's (field programmable gate arrays) and ASIC's (application specific integrated circuits).

Output/encoder 910 receives one or more stimulation parameters from charge-to-waveform parameter converter 905 and outputs them to waveform generator 915 in a form that is usable by waveform generator 915 for the generation of a stimulation waveform. In general, this use will result in waveform generator 915 generating waveforms that are in accordance with the one or more stimulation parameters.

Waveform generator 915 generates a stimulation waveform to stimulate tissue. Waveform generator 915 can be connected to electrodes 205, 207 by leads 229, 227 (not shown) to deliver the stimulation waveform. Waveform generator 915 can be programmable in that a stimulation pulse output by generator 915 is in accordance with the one or more stimulation parameters received from output/encoder 910.

In operation, decoder/receiver 215 can receive a charge setting over a data link such as data link 140. Decoder/receiver 215 relays the charge setting to charge-to-waveform parameter converter 905 in a form suitable for conversion. Converter 905 receives the charge setting and coverts it into one or more stimulation parameters which are relayed to output/encoder 910. Output/encoder 910 programs waveform generator 915 with the stimulation parameters. Waveform generator 915 then outputs a stimulation waveform across electrodes 205, 207 that is in accordance with the programming.

Figures 10, 11, 12:
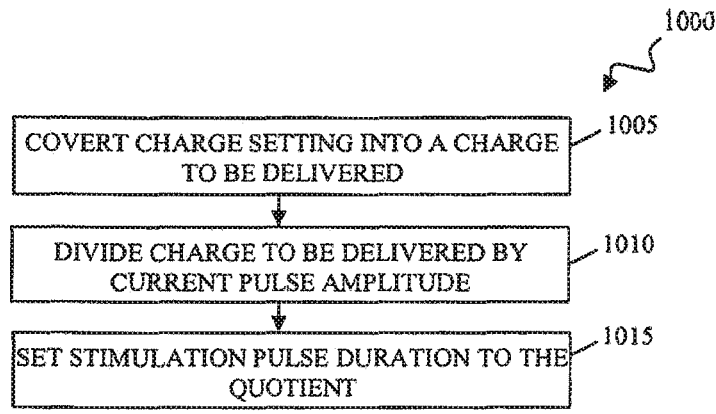
FIG. 10 shows a process for the conversion of a charge setting into a stimulation parameter.
FIGS. 11 and 12 show data compilations for use in the conversion of a charge setting into a stimulation parameter.

FIG. 10 shows a process 1000 for the conversion of a charge setting into one or more stimulation parameters. Process 1000 can operate on discretely or continuously variable charge settings, as discussed below. Process 1000 can be performed in isolation or process 1000 can be performed as a part of another process. For example, process 1000 can be performed as a part of processes 700, 800 (FIGS. 7, 8).

If needed, the system performing process 1000 can convert a charge setting into a charge that is to be delivered at

1005. The exact nature of this conversion will depend on the form of the charge setting. For example, when the charge setting is an incremental increase or decrease of a system-defined setting, the conversion can include determining the charge that is to be delivered from a look-up table or other memory device that associates defined settings with magnitudes of charges to be delivered. As another example, when the charge setting is a percent increase in the charge presently delivered, the conversion can include determining the new magnitude of the charge to be delivered. As yet another example, when the charge setting itself is the new magnitude of the charge that is to be delivered, no conversion is needed.

The system can divide the charge to be delivered by the current pulse amplitude at 1010 and then set the stimulation pulse duration to the quotient at 1015. For example, when primary pulse amplitude parameter 315 characterizes the current amplitude of primary stimulation pulses 305 in waveform 300, pulse duration 320 can be approximated by:

$$\text{pulse duration } 320 \approx (\text{pulse amplitude } 315)/Q \qquad \text{Equation 3}$$

where Q represents the amount of charge to be delivered. As another example, when primary pulse amplitude parameter 315 characterizes the voltage amplitude of primary stimulation pulses 305 in waveform 300, pulse duration 320 can be approximated by:

$$\text{pulse duration } 320 \approx (Z)(Q)/\text{pulse amplitude } 315. \qquad \text{Equation 4}$$

where Z represents the impedance and Q represents the amount of charge to be delivered. Equations 3 and 4 can be adjusted to accommodate various forms of pulse amplitude 315 and impedance Z.

In some implementations, pulse amplitude 315 can be maintained at a maximum possible and/or allowable value at all times during stimulation. The maximum value of pulse amplitude 315 can be determined by the physical constraints of the equipment. The maximum value of pulse amplitude 315 can alternatively be set, e.g., by medical personnel or other users. This setting can take into account the arrangement and/or application of the stimulator.

The system performing process 1000 can also calculate (not shown) a new pulse amplitude and a new pulse duration for secondary recovery pulses 310. These calculations can yield a balanced-charge biphasic waveform in which substantial charge does not, over time, accumulate at the interface of the stimulating electrode and the body.

FIG. 11 shows a data compilation 1100 for use in the conversion of a discretely variable charge setting into one or more stimulation parameters. Data compilation 1100 can be stored in a system for electrically stimulating tissue. For example, data compilation 1100 can be stored in memory 135 (FIG. 1) and/or in memory 225 (FIG. 2). The memory that stores compilation 1100 can be non-volatile and programmed using equipment that is unavailable to non-medical personnel. For the sake of convenience, data compilation 1100 is shown as a table. Other compilations, including hardwired data storage, ROM data storage, data objects, records, files, lists, and multiple compilations that are arranged differently are possible.

Data compilation 1100 includes a charge setting column 1105, a stimulation pulse amplitude column 1110, and a stimulation pulse duration column 1115. Stimulation pulse duration column 1115 identifies one or more discrete stimulation pulse duration values N. Stimulation pulse amplitude column 1110 identifies one or more discrete stimulation pulse amplitude values M. Charge setting column 1105 identifies one or more discrete stimulation pulse charge setting values. In particular, the number of charge setting values identified in column 1105 is less than or equal to the product N*M.

Data compilation 1100 can also identify values of other pulse parameters. For example, data compilation 1100 can identify pulse amplitude values and pulse duration values for secondary recovery pulses 310 (not shown). The additional values can yield a balanced-charge biphasic waveform in which charge does not, over time, accumulate at the interface of the stimulating electrode and the body.

In operation, a processor, memory interface, or other charge-to-waveform parameter converter can access data compilation 1100 to convert a discrete charge setting into one or more stimulation parameters. The conversion can thus be a table look-up or other access of data compilation 1100 in which a charge setting is used to identify stored waveform parameters.

FIG. 12 shows a data compilation 1200 for use in the conversion of a discretely variable charge setting into one or more stimulation parameters. Data compilation 1200 can be stored and represented as described regarding compilation 1100 (FIG. 11) The memory that stores compilation 1200 can be non-volatile and programmed using equipment that is unavailable to non-medical personnel.

Data compilation 1200 includes charge setting column 1105, stimulation pulse amplitude column 1110, and stimulation pulse duration column 1115. For comparatively low charge settings 1205, 1210, stimulation pulse duration column 1115 includes one or more records 1215 that identify that the stimulation pulse duration is to be maintained at a "trip duration." For comparatively high charge settings 1220, 1225, stimulation pulse amplitude column 1110 includes one or more records 1230 that identify that the stimulation pulse duration is to be maintained at a "trip amplitude."

As illustrated, charge setting column 1105 includes one or more intermediate charge settings 1235, 1240 where neither the trip amplitude nor the trip duration is identified. However, this need not be the case and comparatively low charge settings 1205, 1210 can be followed directly by comparatively high charge settings 1220, 1225.

Figure 13:
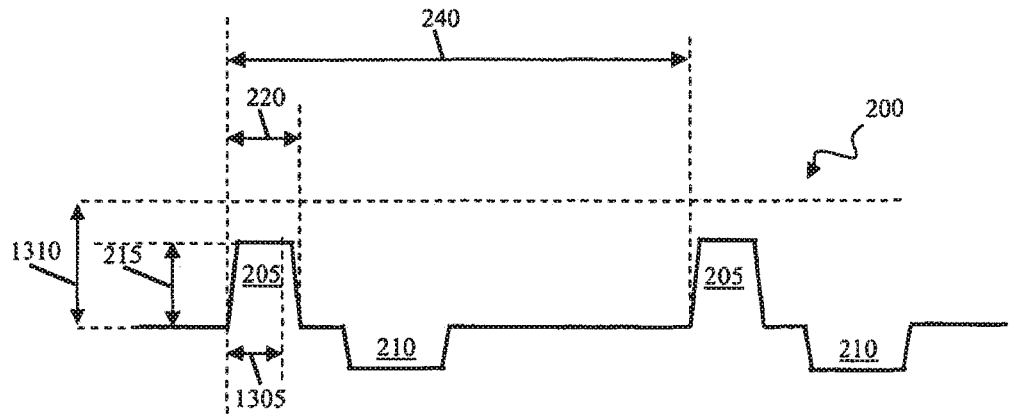
FIG. 13 shows a trip duration and a trip amplitude on the waveform of FIG. 3.

FIG. 13 shows waveform 200 with a trip duration 1305 and a trip amplitude 1310. Trip duration 1305 is the shortest possible or allowable duration of a stimulation pulse 205. Trip amplitude 1310 is largest possible or allowable current or voltage amplitude of a stimulation pulse 205. The illustrated stimulation pulses 205 have a duration 220 that exceeds trip duration 1305 and a pulse amplitude 215 that is less than trip amplitude 1310. Thus, the charge setting for the illustrated waveform 200 is one of the intermediate charge settings 1235, 1240.

In some implementations, trip duration 1305 can be between 50 µs less than the chronaxie time and 200 µs more than the chronaxie time of tissue to be stimulated. For example, trip duration 1305 can be between about 50 µs and 300 µs, such as about 100 µs. In other implementations, trip duration 1305 can be larger, e.g., up to 500 ms. In some implementations, trip amplitude 1310 can be the largest amplitude that the stimulator can provide. For example, when stimulation waveform 200 is shown in terms of current amplitude, is trip amplitude 1310 can be about 50 mA, or about 10 mA.

In some implementations, data compilation 1200 can indicate that a stimulator, for increasing charge settings, is to stimulate at trip duration 1305 with increasing amplitudes 215 until trip amplitude 1310 is reached. When trip amplitude 1310 is reached, data compilation 1200 can indicate that the stimulator is to stimulate at trip amplitude 1310 with increasing pulse durations 220. The charge setting for this transition between holding pulse duration 220 at trip duration 1305 and holding amplitude 215 at trip amplitude 1310 can be, e.g., about 1000 nC.

Figure 14:
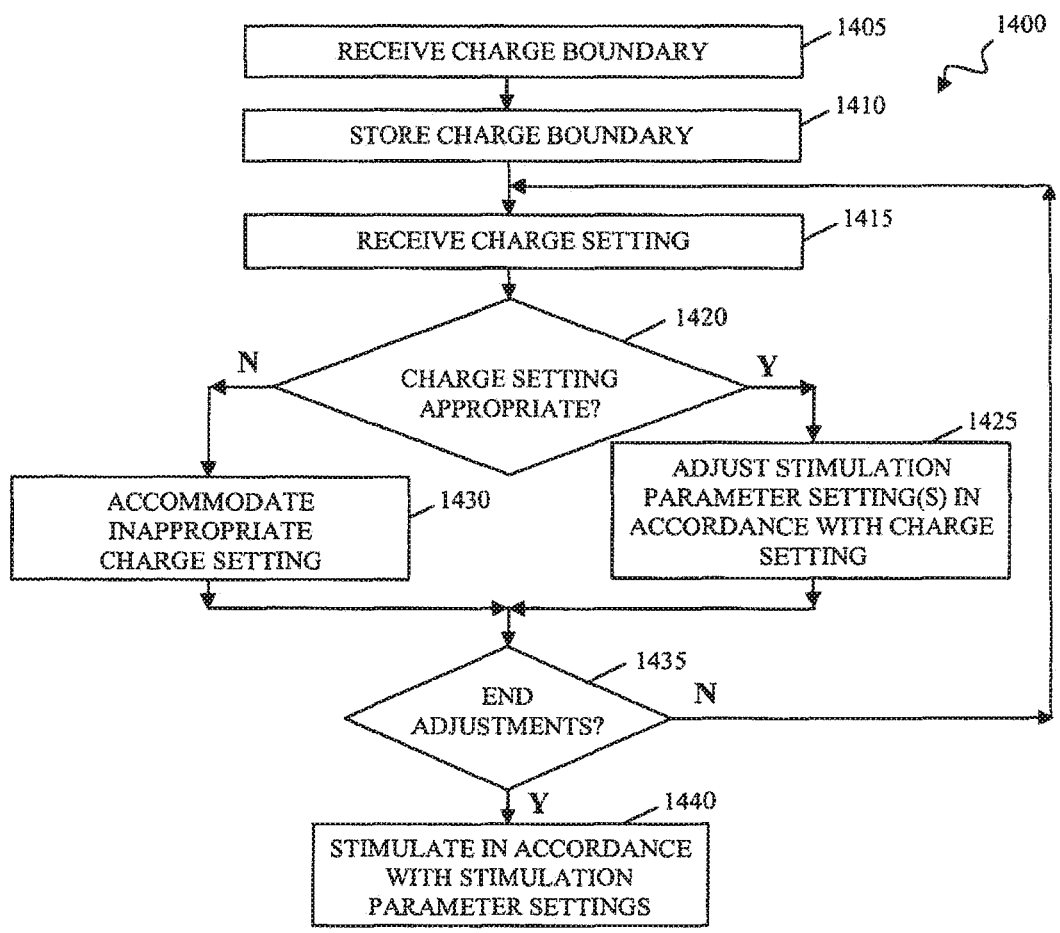
FIGS. 14 and 15 show processes for controlling charge flow during the electrical stimulation of tissue.

FIG. 14 shows a process 1400 for controlling charge flow during the electrical stimulation of tissue. Process 1400 can be performed by a system for stimulating tissue such as system 100. Process 1400 can be performed in isolation or process 1400 can be performed as part of a larger process. For example, process 1400 can be performed in conjunction with either of processes 700, 800. In conjunction with processes 700, 800, process 1400 can be performed at either the external portion or the stimulator.

The system performing process 1400 can receive one or more charge boundaries at 1405. A charge boundary can identify the highest amount of charge that is to flow during a stimulation pulse. A second charge boundary can identify the lowest amount of charge that is to flow during a stimulation pulse. A charge boundary can reflect the technical characteristics of a stimulator or a charge boundary can reflect a limit set by medical personnel or a device designer to tailor the electrical stimuli to certain ends. Extreme values can be identified either as the values themselves (i.e., the maximum value is 5.0) or using comparisons (i.e., the maximum value must be less than 5.0). A charge boundary can be received from a user such as a medical professional. For example, a charge boundary can be received over a user interface such as user interface 115 (FIG. 1) and/or input elements 415 of housing 400 of external portion 110 (FIG. 4).

The system can also store the charge boundary at 1410. The charge boundary can be stored in a memory such as memory 135 of external portion 110 (FIG. 1) and/or memory 225 of stimulator 200 (FIG. 2).

The system can also receive a charge setting at 1415. The charge setting can identify a relative change in an amount of charge or the amount of charge that is to be delivered during a stimulation pulse. The charge setting can be received over a user interface such as charge setting components 405 (FIG. 4).

The system can determine if the received charge setting is appropriate at 1420. Determining if the charge setting is appropriate can include comparing the charge setting to the one or more stored charge boundaries to ensure that the proposed adjustment is within the charge boundaries.

If the system determines that the charge setting is appropriate, then the system can adjust one or more stimulation parameter settings in accordance with the charge setting at 1425. This adjustment can include converting the charge setting into one or more stimulation parameter settings as discussed above.

On the other hand, if the system determines that the proposed charge setting is inappropriate, the system can accommodate the inappropriate adjustment at 1430. For example, an inappropriate charge setting can be discarded, the user informed of the discard, and operations continued using a previous charge setting. As another example, an inappropriate charge setting can be changed to the violated charge boundary, the user informed of the change, and one or more stimulation parameter settings can be adjusted in accordance with the charge boundary.

With a stimulation parameter setting adjusted or an inappropriate adjustment accommodated, the system can determine if changes to the charge setting are to end at 1435. This determination can be made based on a number of different factors including user input indicating that adjustments are to end or a lack of user input over time.

If the system determines that adjustments are indeed to end, then the system can stimulate in accordance with the existing stimulation parameter settings at 1440. However, if adjustments are not going to end, then the system can receive an additional charge setting at 1415.

Figure 15:
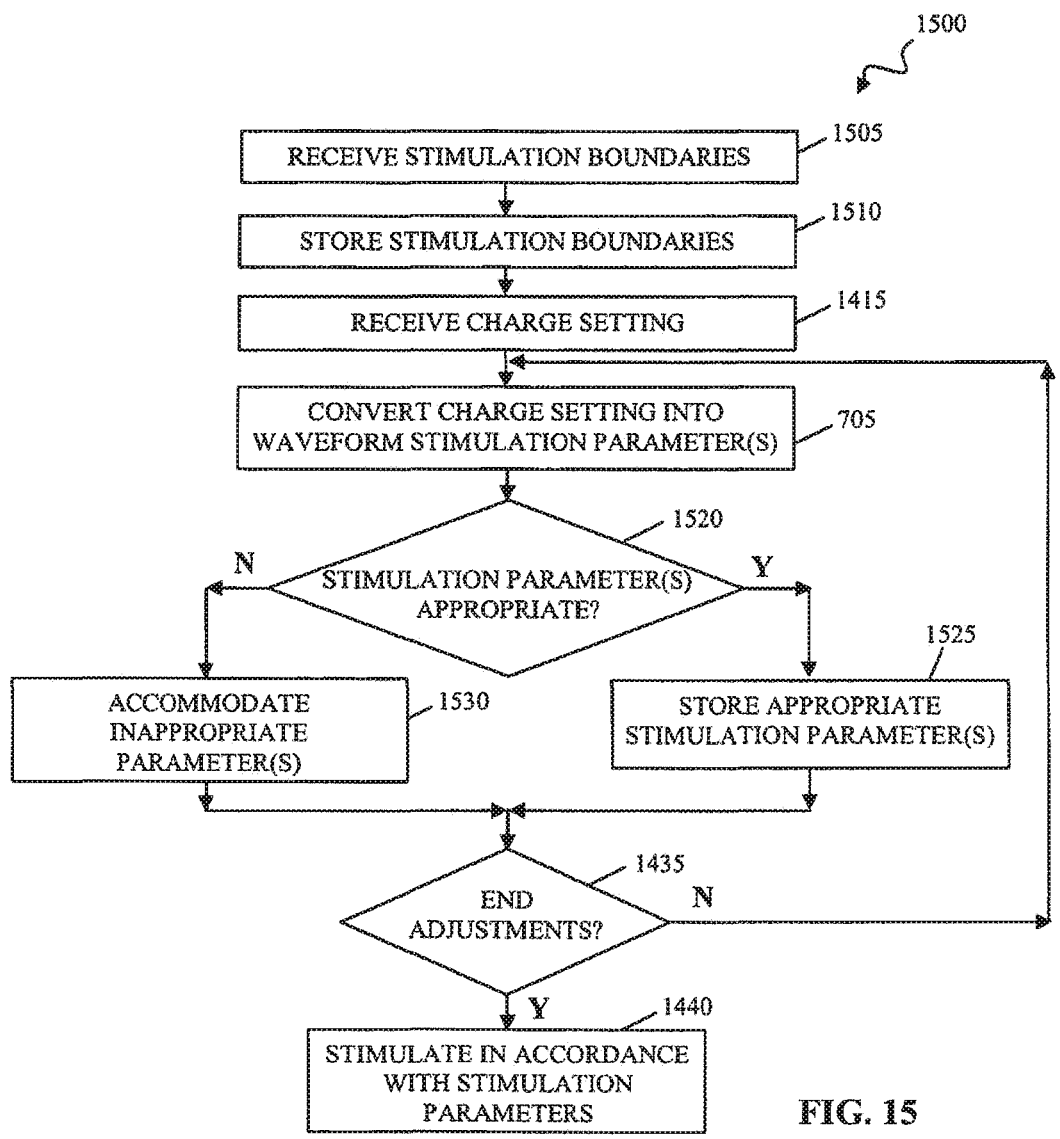

FIG. 15 shows a process 1500 for controlling charge flow during the electrical stimulation of tissue. Process 1500 can be performed by a system for stimulating tissue such as system 100. Process 1500 can be performed in isolation or process 1500 can be performed as part of a larger process. For example, process 1500 can be performed in conjunction with either of processes 700, 800. In conjunction with processes 700, 800, process 1500 can be performed at either the external portion or the stimulator.

The system performing process 1500 can receive one or more stimulation boundaries at 1505. A stimulation boundary is an extreme allowable value of a stimulation parameter. The stimulation boundaries can identify the extreme allowable value(s) of one or more stimulation parameters, such as parameters 315, 320, 325, 330, 335, 340, 345 (FIG. 3). Trip duration 1305 and trip amplitude 1310 (FIG. 13) are thus stimulation boundaries. A stimulation boundary can reflect the technical characteristics of a stimulator or a stimulation boundary can reflect a limit set by medical personnel or a device designer to tailor the electrical stimuli to certain ends. Extreme values can be identified either as the values themselves (i.e., the maximum value is 5.0) or using comparisons (i.e., the maximum value must be less than 5.0). The stimulation boundaries can be received over a user interface such as user interface 115 (FIG. 1).

The system can also store the received stimulation boundaries at 1510. The stimulation boundaries can be stored in memory 135 in external portion 110 of system 100 (FIG. 1). The stimulation boundaries can also be stored in memory 225 in stimulator 200 (FIG. 2).

The system performing process 1500 can also receive a charge setting at 1415 and convert the charge setting into one or more waveform stimulation parameters at 705.

The system can also determine if the one or more waveform stimulation parameters are appropriate at 1520. Determining if the stimulation parameters are appropriate can include comparing the stimulation parameters to one or more stored stimulation boundaries to ensure that the stimulation parameters are within the stimulation boundaries.

If the system determines that the stimulation parameters are appropriate, then the system can store the appropriate parameters at 1525. For example, appropriate stimulation parameters can be stored in memory 225 in stimulator 200 (FIG. 2).

On the other hand, if the system determines that the stimulation parameters are inappropriate, the system can accommodate the inappropriate stimulation parameters at 1530. For example, an inappropriate stimulation parameter can be discarded, the user informed of the discard, and operations continued using a previous stimulation parameter. As another example, an inappropriate stimulation parameter can be changed to the violated stimulation boundary, the user informed of the change, and operations continued using the changed stimulation parameter. As yet another example, an inappropriate stimulation parameter can be stored as if it were appropriate. However, the stimulation that is actually delivered can be controlled by a device such as a voltage or current limiter that prevents the delivered stimulation from actually violating the stimulation boundary.

With an appropriate stimulation parameter stored or an inappropriate parameter accommodated, the system can determine if changes to the charge setting are to end at 1435. If the system determines that adjustments are indeed to end, then the system can stimulate in accordance with the existing stimulation parameter settings at 1440. However, if adjustments are not going to end, then the system can receive an additional charge setting at 1415.

Figures 16, 17:
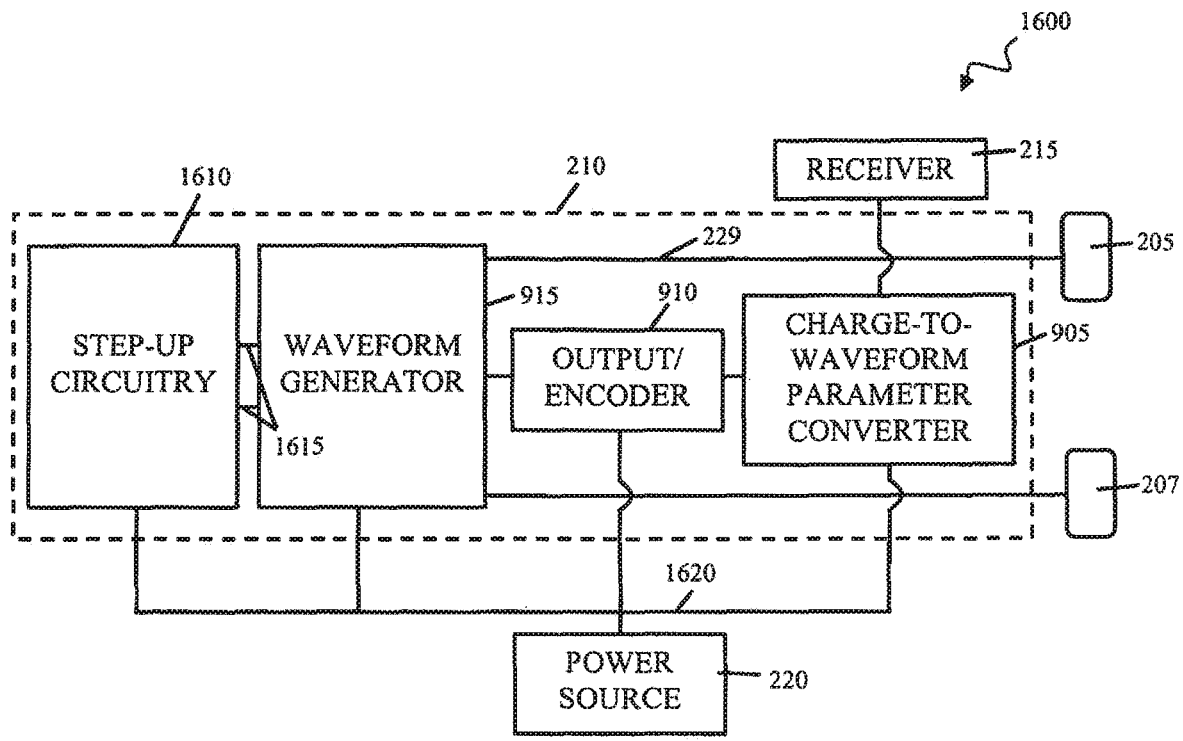
FIG. 16 shows a block diagram of the stimulator of FIG. 2 in which charge flow is controlled during stimulation.
FIG. 17 shows a data compilation for use in the conversion of a charge setting into a stimulation parameter.

FIG. 16 shows a block diagram of one implementation of a stimulator 200 in which charge flow is controlled during stimulation. In addition to charge-to-waveform parameter converter 905, output/encoder 910, and waveform generator 915, electrical circuitry 210 includes step-up circuitry 1610. Step-up circuitry 1610 includes one or more devices that increases the potential difference output by power source 220 for use in stimulating tissue. In particular, step-up circuitry 1610 outputs a higher potential difference on lines 1615 to waveform generator 915 than step-up circuitry 1610 receives on a supply line 1620 from source 220. Step-up circuitry 1610 can include, e.g., voltage converter circuitry, charge pump circuitry, and the like.

In operation, receiver 215 can receive a charge setting over a data link such as data link 140. Receiver 215 relays the charge setting to charge-to-waveform parameter converter 905. Converter 905 receives the charge setting and coverts it into one or more stimulation parameters which are relayed to output/encoder 910. Output/encoder 910 programs waveform generator 915 with the stimulation parameters.

Output/encoder 910 can program waveform generator 915 with stimulation parameters that call for waveform generator 915 to output a waveform that includes voltage differences in excess of a supply voltage provided on supply line 1620 by power source 220. In these cases, waveform generator 915 can be supplied by step-up circuitry 1610 to generate the voltage differences in excess of the supply voltage. Waveform generator 915 can then output a stimulation waveform across electrodes 205, 207 that is in accordance with the programming.

FIG. 17 shows a data compilation 1700 for use in the conversion of a discretely variable charge setting into one or more stimulation parameters.

Data compilation 1700 is adapted for use with stimulators 200 that include certain classes of step-up circuitry, such as step-up circuitry 1610 (FIG. 16). In particular, data compilation 1700 is adapted for use with stimulators 200 that include classes of step-up circuitry that generate discrete "steps-up" in voltage.

One example of such step-up circuitry is charge pump circuitry that generates one or more discrete voltage steps (at least one of which is in excess of the supply voltage). These voltage steps can be used to define discrete voltage amplitudes of stimulation or other pulses. Another example of such step-up circuitry is voltage converter circuitry that outputs one or more discrete voltage steps that are the product of supply or other voltages and one or more discrete factors. For example, voltage converter circuitry may be able to generate a discrete voltage of two times the supply voltage. These discrete voltage steps can be used to define discrete voltage amplitudes of stimulation or other pulses. Yet another example is a combination of step-up circuitry with voltage converter circuitry. One or more discrete voltage steps output by step-up circuitry can be input into voltage converter circuitry, where it is multiplied by one or more discrete factors to generate discrete voltage steps. Such discrete voltage steps can be used to define discrete voltage amplitudes of stimulation or other pulses.

Data compilation 1700 includes charge setting column 1105, stimulation pulse amplitude column 1110, and stimulation pulse duration column 1115. Stimulation pulse amplitude column 1110 includes groups of two or more records 1705, 1710 that identify that the stimulation pulse duration is to be maintained at voltage amplitudes that correspond to the voltage steps generated by the charge pump circuitry. For example, records 1705 identify that the same voltage step 1 (with different durations) is to be used with two different charges. Similarly, records 1710 identify that the same voltage step 2 (with different durations) is to be used with two different charges.

By setting the stimulation pulse amplitude to about the same level as the voltage step, the efficiency of the step-up circuitry is increased. In particular, there is no voltage loss associated with a reduction of the voltage step to a lower voltage. Rather, the voltage step can be used directly to generate a stimulation pulse.

Figure 18:
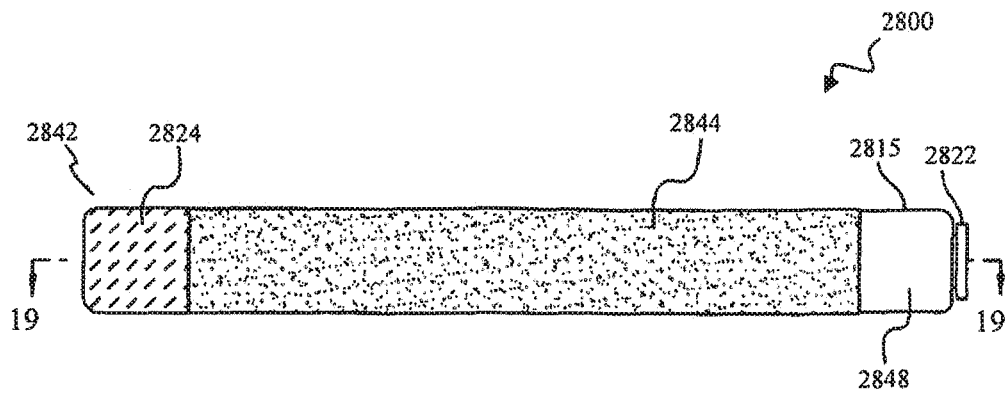
FIGS. 18, 19, and 20 show another implementation of an implanted portion of the system of FIG. 1.
Figure 19:
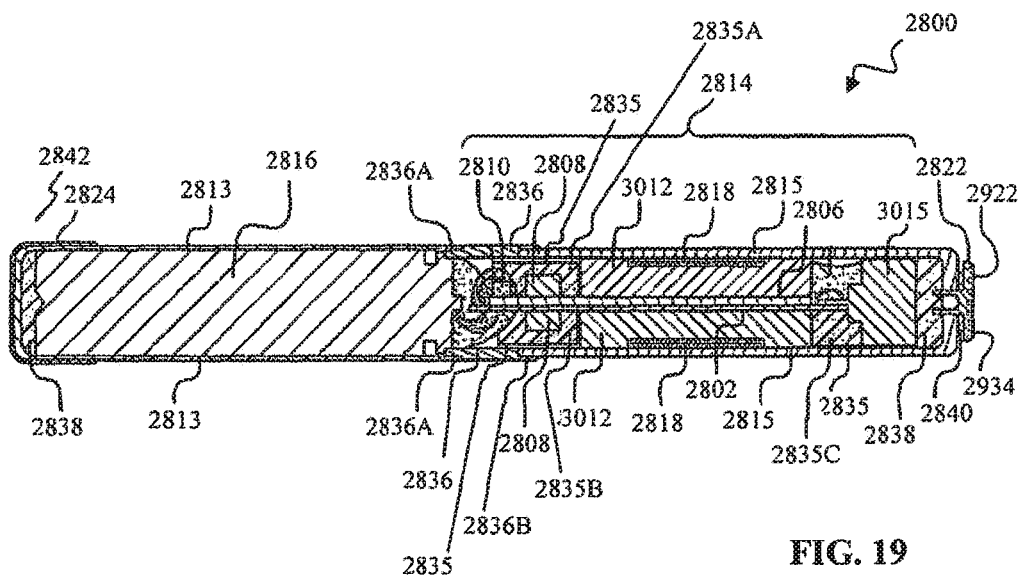
Figure 20:
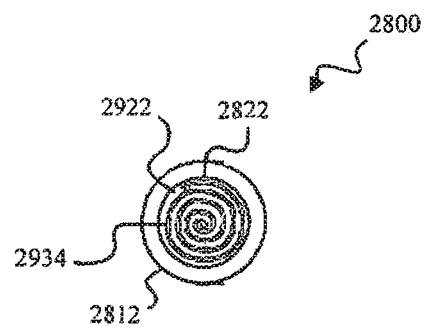

FIGS. 18, 19, and 20 show another implementation of implanted portion 105, namely a stimulator 2800. In particular, FIG. 18 shows a side view of stimulator 2800, FIG. 19 shows a sectional view of stimulator 2800 along the line 19-19 in FIG. 18, and FIG. 20 shows an end view of stimulator 2800.

Stimulator 2800 includes electrodes 2822 and 2824, a power source 2816, electronic subassembly 2814, and a case 2812. Electrode 2822 is an active/stimulating electrode whereas electrode 2824 is an indifferent/reference electrode. Electrodes 2822 and 2824 can be made from any of the materials discussed above.

Power source 2816 provides power for the operation of stimulator 2800, including the delivery of electrical stimuli to tissue through electrodes 2822 and 2824. Power source 2816 can be a primary battery, a rechargeable battery, super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is placed in the middle of the long, thin-rod shape of the microstimulator), a bioenergy power source (where a chemical reaction provides an energy source), a fuel cell (much like a battery, but does not run down or require recharging, but requires only a fuel), a bioelectrical cell (where two or more electrodes use tissue-generated potentials and currents to capture energy and convert it to useable power), an osmotic pressure pump (where mechanical energy is generated due to fluid ingress), or the like.

When power source 2816 is a battery, it can be a lithium-ion battery or other suitable type of battery. When power source 2816 is a rechargeable battery, it can be recharged from an external system through a power link such as power link 145 (FIG. 1). One type of rechargeable battery that can be used is disclosed in International Publication WO 01/82398 A1, published 1 Nov. 2001, and/or WO 03/005465 A1, published 16 Jan. 2003, the contents of both of which are incorporated herein by reference. Other battery construction techniques that can be used to make power source 2816 include those shown, e.g., in U.S. Pat. Nos. 6,280,873; 6,458,171, and U.S. Publications 2001/0046625 A1 and U.S. 2001/0053476 A1, the contents of all of which are also incorporated herein by reference. Recharging can be performed using an external charger.

Electronic subassembly 2814 includes a coil 2818 and a stimulating capacitor 3015. Electrode 2822 is coupled to electronic subassembly 2814 through stimulating capacitor 3015. The coil 2818 can receive power for charging power source 2816 using power received over power link 145 (FIG. 1).

Electronic subassembly 2814 can also include circuitry for stimulation, battery charging (when needed), telemetry, production testing, and behavioral control. The stimulation circuitry can be further divided into components for high voltage generation, stimulation phase current control, recovery phase current control, charge balance control, and over voltage protection circuitry. The telemetry circuitry can be further divided into an OOK receiver, FSK receiver, and FSK transmitter. The behavioral control circuitry can be further divided into components for stimulation timing, high voltage generation closed loop control, telemetry packet handling, and battery management. In addition to these functions, there is circuitry for reference voltage and reference current generation, system clock generation, and Power-On Reset (POR) generation.

In operation, charging circuitry within electronic subassembly 2814 can detect the presence of an external charging field. Upon detection, stimulator 2800 can receive a telemetry message and recharge power source 2816, as necessary. The electronic subassembly 2814 can measure a rectified voltage during recharging and transmit the measured voltage value to an external device over a data link such as link 140 (FIG. 1). Battery voltage measurements can be made at times when stimulation pulses are not being delivered. U.S. Pat. No. 6,553,263, incorporated herein by reference, describes charging technology that also can be used.

When power source 2816 used within stimulator 2800 is something other than a rechargeable battery, e.g., a primary battery and/or one of the alternative power sources described previously, then the electronic subassembly 2814 can be modified appropriately to interface with, control and/or monitor whatever power source is used. For example, when power source 2816 comprises a primary battery, electronic subassembly 2814 can be simplified to include only monitoring circuitry and exclude charging circuitry. Such monitoring circuitry can provide status information regarding how much energy remains stored within the primary battery to provide the physician and/or patient an indication of the remaining life of the battery.

As another example, when power source 2816 used within stimulator 2800 is a super capacitor used in combination with a primary battery and/or a rechargeable battery, electronic subassembly 2814 can use the charge stored on the super capacitor to power stimulator 2800 during times of peak power demand. Such times include times when telemetry signals are being transmitted from stimulator 2800 to one or more external device(s), or when the amplitude of the stimulation pulses has been programmed to be relatively high. When used in combination with a rechargeable battery, electronic subassembly 2814 can use the charge stored on the super capacitor to recharge the rechargeable battery or to power stimulator 2800 at times of high power demand.

Electronic subassembly 2814 can also include protection circuitry to act as a failsafe against battery over-voltage. A battery protection circuit can continuously monitor a battery's voltage and electrically disconnect the battery if its voltage exceeds a preset value.

Electronic subassembly 2814 can also include a coulomb counter, a waveform generator, a charge-to-waveform parameter converter, an output/encoder, a memory, step-up circuitry, a processor and/or other electronic circuitry that allow it to generate stimulating pulses that are applied to a patient through electrodes 2822 and 2824 in accordance with logic located within the electronic subassembly 2814. The processor and/or other electronic circuitry can also control data communication with an external portion such as external portion 110 (FIG. 1). The processor and/or other electronic circuitry can allow stimulator 2800 to perform processes described above in FIGS. 5, 7, 8, 10, 14, 15.

Electronic subassembly 2814 can also include a panel 2802, integrated circuitry 2806, capacitors 2808, diodes 2810, and two ferrite halves 3012. The arrangement of these components in electronic subassembly 2814 is described in U.S. Patent Publication No. 2005/0021108, the contents of which are incorporated herein by reference.

Case 2812 can have a tubular or cylindrical shape with an outer diameter greater than about 3.20 mm and less than about 3.7 mm. For example, case 2812 can have an outer diameter of about 3.30 mm. Case 2812 can have an inner diameter that encloses electronic subassembly 2814 of greater than about 2.40 mm and less than about 2.54 mm. Case 2812 can have an inner diameter that encloses power source of greater than about 2.92 mm and less than about 3.05 mm. The length of case 2812 can be less than about 30 mm, and less than about 27 mm. The portion of case 2812 that encloses electronic subassembly 2814 can be less than about 13.00 mm in length. The portion of case 2812 that encloses power source 2816 that encloses power source 2816 can be about 11.84 mm in length. These dimensions are only examples and can change to accommodate different types of batteries or power sources. For example, stimulator 2800, instead of being cylindrically shaped, can have a rectangular, asymmetrical, or ovoid cross section. Case 2812 can be Magnetic Resonance Imaging (MM) compatible.

Case 2812 is sealed to protect electrical components inside stimulator 2800. For example, case 2812 can be hermetically-sealed and made from two cylindrical cases, namely, a titanium 6/4 case 2813 and a zirconia ceramic case 2815. Other materials and shapes for the housing can also be used. A titanium 6/4 or other suitable connector 2836 can be brazed with a titanium nickel alloy (or other suitable material) to ceramic case 2815 for securing the mating end of titanium case 2813. A connector 2836 has an inside flange 2836A and an outside flange 2836B which serve to "self center" the braze assembly. Before inserting the subassembly and before securing the mating ends, conductive silicone adhesive 2838 can be applied to the inside end of the ceramic shell as well as to the inside end of the titanium shell. A molecular sieve moisture getter material 2835 is also added to areas 2835A, 2835B, and 2835C (FIG. 19) before the brazing process.

The "spiral" self centering button electrode 2822 can be made from titanium 6/4 or other suitable material and plated with an iridium coating or other suitable conductive coating. An end view of electrode 2822 is shown in FIG. 20. A spiral groove 2924 can be made in stimulating surface 2922 of the electrode 2822. Other groove shapes, such as a cross hatch pattern or other patterns can also be used to increase the conductive surface area 2922 of electrode 2822.

The sharp edges in groove 2924 can force a more homogeneous current distribution over the surface 2922 and decrease the likelihood of electrode corrosion over time by reducing current density along the sharp groove edges. A tool made in the shape of a trapezoid or similar shape can be used to cut the groove 2924 into a spiral or other shape. Other devices for cutting the groove 2924 can be used such as, e.g., ion beam etching.

The button electrode 2822 can act as active or stimulating electrode. A titanium/nickel alloy 2840 or other suitable material can be used to braze the button electrode 2822 to the zirconia ceramic case 2815. An end view of the stimulator 2800 is shown in FIG. 20 where the end view of the stimulating "spiral" button electrode 2822 can be seen. The end 2842 of the titanium shell 2813 can be plated with an iridium coating (other suitable conductive coating can be applied), which plated area becomes the indifferent iridium electrode 2824.

FIG. 18 shows a top view of stimulator 2800 with the external coatings depicted. A type C parylene or other suitable electrically insulating coating can be applied to the shaded area 2844, e.g., by standard masking and vapor deposition processes. The zirconia ceramic case is left exposed in area 2848 and the iridium electrode 2824 is shown on the end 2842 of the titanium case 2813.

U.S. Pat. No. 6,582,441, incorporated herein by reference, describes a surgical insertion tool which can be used for implanting stimulator 2800. The procedures taught in the '441 patent for using the tool and associated components can be used for implanting and extracting stimulator 2800. The surgical insertion tool described in the '441 patent facilitates the implantation of stimulator 2800 in a patient so that stimulating electrode 2822 is proximate to a nerve site (e.g., near the pudendal nerve for treating patients with urinary urge incontinence). The distance between electrode 2822 and the nerve site can be, for example, less than 1-2 mm.

Other implantation procedures exist relating to the specific area to be stimulated. The stimulator 2800 can also be implanted in other nerve sites relating to preventing and/or treating various disorders associated with, e.g., prolonged inactivity, confinement or immobilization of one or more muscles and/or as therapy for various purposes including paralyzed muscles and limbs, by providing stimulation of the cavernous nerve(s) for an effective therapy for erectile or other sexual dysfunctions, and/or by treating other disorders, e.g., neurological disorders caused by injury or stroke.

A number of implementations have been described. Nevertheless, it will be understood that various modifications may be made without. For example, the described systems and techniques can be applied to electrical stimulators that are wholly extracorporeal. Other implementations are within the scope of the following claims.

What is claimed is:

1. An implantable medical device, comprising:
   a plurality of electrodes;
   control circuitry configured to:
      receive a charge setting value that is expressed in Coulombs; and
      convert the charge setting value into one or more stimulation parameters; and
   a waveform generator configured to generate a stimulation waveform from the one or more stimulation parameters at one or more of the plurality of the electrodes to provide the stimulation waveform to a patient.

2. The implantable medical device of claim 1, further comprising a receiver configured to receive the charge setting value from an external controller and to provide the charge setting value to the control circuitry.

3. The implantable medical device of claim 1, wherein the control circuitry configured to convert the charge setting value into one or more stimulation parameters comprises control circuitry configured to determine a pulse duration based on the charge setting value and a stimulation current amplitude.

4. The implantable medical device of claim 1, wherein the control circuitry configured to convert the charge setting value into one or more stimulation parameters comprises control circuitry configured to determine a pulse duration based on the charge setting value, a stimulation voltage amplitude, and an impedance value.

5. The implantable medical device of claim 4, wherein the impedance value is a measured impedance between the one or more of the electrodes.

6. The implantable medical device of claim 4, wherein the impedance value is an estimated value.

7. The implantable medical device of claim 1, wherein the control circuitry configured to convert the charge setting value into one or more stimulation parameters comprises control circuitry configured to retrieve the one or more stimulation parameters from a data compilation using the charge setting value.

8. The implantable medical device of claim 1, wherein the one or more stimulation parameters comprise a primary pulse amplitude and a primary pulse duration.

9. The implantable medical device of claim 8, wherein the stimulation waveform is a balanced-charge stimulation waveform and wherein the one or more stimulation parameters further comprise a secondary pulse amplitude and a secondary pulse duration for a recovery pulse.

10. A method for operating an implantable medical device comprising a plurality of electrodes, the method comprising:
    receiving a charge setting value that is expressed in Coulombs;
    converting the charge setting value into one or more stimulation parameters; and
    programming a waveform generator in the implantable medical device to generate a stimulation waveform using the one or more stimulation parameters at one or more of the plurality of the electrodes to provide the stimulation waveform to a patient.

11. The method of claim 10, wherein the charge setting value is received at an external controller.

12. The method of claim 11, wherein the external controller transmits the charge setting value to the implantable medical device.

13. The method of claim 12, wherein the implantable medical device converts the charge setting value into the one or more stimulation parameters.

14. The method of claim 13, wherein the one or more stimulation parameters are retrieved in the implantable medical device from a data compilation using the charge setting value.

15. The method of claim 11, wherein the external controller converts the charge setting value into the one or more stimulation parameters.

16. The method of claim 15, wherein the external controller transmits the one or more stimulation parameters to the implantable medical device.

17. The method of claim 10, wherein the one or more stimulation parameters comprise a pulse duration and a stimulation current amplitude based on the charge setting value.

18. The method of claim 10, wherein the one or more stimulation parameters comprise a pulse duration based on the charge setting value, a stimulation voltage amplitude, and an impedance value.

* * * * *